(12) United States Patent
Clark et al.

(10) Patent No.: US 7,790,940 B2
(45) Date of Patent: Sep. 7, 2010

(54) LIQUID PHASE ALKYLATION PROCESS

(75) Inventors: Michael C. Clark, Chantilly, VA (US); Frederick Y. Lo, Middlesex, NJ (US); Christine N. Elia, Bridgewater, NJ (US); Matthew J. Vincent, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 554 days.

(21) Appl. No.: 11/820,907

(22) Filed: Jun. 21, 2007

(65) Prior Publication Data

US 2008/0319242 A1 Dec. 25, 2008

(51) Int. Cl.
*C07C 2/66* (2006.01)
(52) U.S. Cl. ...................................... 585/467
(58) Field of Classification Search .................. 585/467
See application file for complete search history.

(56) References Cited

U.S. PATENT DOCUMENTS

| | | | |
|---|---|---|---|
| 3,751,504 A | 8/1973 | Keown et al. | |
| 4,016,218 A | 4/1977 | Haag et al. | |
| 4,459,426 A | 7/1984 | Inwood et al. | |
| 4,547,605 A | 10/1985 | Kresge et al. | |
| 4,891,458 A | 1/1990 | Innes et al. | |
| 4,992,606 A | 2/1991 | Kushnerick et al. | |
| 5,149,894 A | 9/1992 | Holtermann et al. | |
| 5,334,795 A | 8/1994 | Chu et al. | |
| 5,557,024 A | 9/1996 | Cheng et al. | |
| 5,600,050 A | 2/1997 | Huang et al. | |
| 6,376,730 B1 | 4/2002 | Jan et al. | |
| 6,710,003 B2 | 3/2004 | Jan et al. | |
| 6,984,764 B1 | 1/2006 | Roth et al. | |
| 2002/0137977 A1 | 9/2002 | Hendriksen et al. | |
| 2004/0138051 A1 | 7/2004 | Shan et al. | |
| 2005/0197517 A1 | 9/2005 | Cheng et al. | |

FOREIGN PATENT DOCUMENTS

| | | |
|---|---|---|
| EP | 0 847 802 | 6/1998 |
| WO | 2006/002805 | 1/2006 |

*Primary Examiner*—Thuan Dinh Dang
(74) *Attorney, Agent, or Firm*—Darryl M. Tyus; Xiaobing Feng

(57) ABSTRACT

The present invention provides an improved process for conversion of feedstock comprising an alkylatable aromatic compound and an alkylating agent to desired alkylaromatic conversion product under at least partial liquid phase conversion conditions in the presence of specific catalyst comprising a porous crystalline material, e.g. a crystalline aluminosilicate, and binder in the ratio of crystal/binder of from about 20/80 to about 60/40. The porous crystalline material of the catalyst may comprise a crystalline molecular sieve having the structure of Beta, an MCM-22 family material, e.g. MCM-49, or a mixture thereof.

7 Claims, No Drawings

LIQUID PHASE ALKYLATION PROCESS

BACKGROUND OF THE INVENTION

The present invention relates to an improved process for producing alkylaromatics, for example, ethylbenzene, cumene and sec-butylbenzene.

Of the alkylaromatic compounds advantageously produced by the present improved process, ethylbenzene and cumene, for example, are valuable commodity chemicals which are used industrially for the production of styrene monomer and coproduction of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equimolar amounts of phenol and acetone. Ethylbenzene may be produced by a number of different chemical processes. One process which has achieved a significant degree of commercial success is the vapor phase alkylation of benzene with ethylene in the presence of a solid, acidic ZSM-5 zeolite catalyst. Examples of such ethylbenzene production processes are described in U.S. Pat. Nos. 3,751,504 (Keown), 4,547,605 (Kresge) and 4,016,218 (Haag).

Another process which has achieved significant commercial success is the liquid phase process for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite beta, whereas U.S. Pat. No. 5,334,795 (Chu) describes the use of MCM-22 in the liquid phase synthesis of ethylbenzene. The latter patent teaches use of catalyst comprising MCM-22 crystalline material and binder in the ratio of crystal/binder of from about 1/99 to about 90/10.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Other publications show use of catalysts comprising crystalline zeolites and binders for conversion of feedstock comprising an alkylatable aromatic compound and an alkylating agent to alkylaromatic conversion product under at least partial liquid phase conversion conditions. These include U.S. 2005/0197517A1 (Cheng) showing use of a catalyst crystal/binder ratio of 65/35 and 100/0; U.S. 2002/0137977A1 (Hendriksen) showing use of a catalyst crystal/binder ratio of 100/0 while noting the perceived negative effect of binders on selectivity; U.S. 2004/0138051A1 (Shan) showing use of a catalyst comprising a microporous zeolite embedded in a mesoporous support, where the zeolite/support ratio is from less than 1/99 to more than 99/1, preferably from 3/97 to 90/10; WO 2006/002805 (Spano) teaching use of a catalyst crystal/binder ratio of 20/80 to 95/5, exemplifying 55/45; U.S. Pat. No. 6,376,730 (Jan) showing use of layered catalyst crystal/binder of 70/30 and 83/17; EP 0847802B1 showing use of a catalyst crystal/binder ratio of from 50/50 to 95/5, preferably from 70/30 to 90/10; and U.S. Pat. No. 5,600,050 (Huang) showing use of catalyst comprising 30 to 70 wt. % H-Beta zeolite, 0.5 to 10 wt. % halogen, and the remainder alumina binder.

Existing alkylation processes for producing alkylaromatic compounds, for example, ethylbenzene and cumene, inherently produce polyalkylated species as well as the desired monoalkylated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

Although it is suggested in the art that catalysts for conversion of feedstock comprising an alkylatable aromatic compound and an alkylating agent to alkylaromatic conversion product under at least partial liquid phase conversion conditions are composed of a porous crystalline aluminosilicate and binder in the ratio of crystal/binder of from 1/99, e.g. 5/95, to 100/0, current commercial catalysts, i.e. those found to be commercially useful, for this process are composed of a porous crystalline aluminosilicate and binder in the ratio of crystal/binder of either 65/35 or 80/20. Finding a commercially acceptable catalyst for such processes conducted under at lease partial liquid phase conversion conditions which increases monoselectivity, i.e. lower di- or polyalkyl product make, would allow capacity expansion in existing plants and lower capital expense for grassroots plants as a result of lower aromatic compound/alkylating agent ratios. According to the present invention, it has now unexpectedly been found that a liquid phase or partial liquid phase alkylation process for producing alkylaromatics conducted in the presence of a specific catalyst comprising a porous crystalline material, e.g. a crystalline aluminosilicate, ("crystal") and binder in the ratio of crystal/binder of from about 20/80 to about 60/40, yields a unique combination of activity and, importantly, monoselectivity. This is especially the case when the process involves at least partial liquid phase alkylation for manufacture of ethylbenzene or cumene. This obviates or lessens the demand in many instances for the difficult transalkylation reaction for conversion of unwanted bulky polyalkylated species in such a process.

SUMMARY OF THE INVENTION

According to the present invention, there is provided an improved process for conversion of a feedstock comprising an alkylatable aromatic compound and an alkylating agent to desired alkylaromatic conversion product under at least partial liquid phase conversion conditions in the presence of specific catalyst comprising a porous crystalline material, e.g. a crystalline aluminosilicate, and binder in the ratio of crystal/binder of from about 20/80 to about 60/40. According to one aspect of the invention, there is provided a process for selectively producing a desired monoalkylated aromatic compound comprising the step of contacting an alkylatable aromatic compound with an alkylating agent in the presence of catalyst under at least partial liquid phase conditions, said catalyst comprising a porous crystalline material, e.g. a crystalline aluminosilicate, and binder in the ratio of crystal/binder of from about 20/80 to about 60/40. Another aspect of the present invention is an improved alkylation process for the selective production of monoalkyl benzene comprising the step of reacting benzene with an alkylating agent under alkylation conditions in the presence of alkylation catalyst which comprises a porous crystalline material, e.g. a crystalline aluminosilicate, and binder in the ratio of crystal/binder of from about 20/80 to about 60/40.

The catalyst for use in the present process may comprise, for example, a crystalline molecular sieve having the structure of zeolite Beta, or one having an X-ray diffraction pattern including d-spacing maxima at 12.4±0.25, 6.9±0.15, 3.57±0.07 and 3.42±0.07 Angstroms. More particularly, the catalyst for use herein may comprise a crystalline molecular sieve having the structure of Beta, an MCM-22 family material, e.g. MCM-22, or a mixture thereof.

The catalyst for use in the present invention preferably comprises an MCM-22 family material, such as for example a crystalline silicate having the structure of MCM-22, PSH-3, SSZ-25, ERB-1, ITQ-1, ITQ-2, ITQ-30, MCM-36, MCM-49, MCM-56, UZM-8 and mixtures thereof.

DETAILED DESCRIPTION OF THE INVENTION

The present invention relates to an improved process for production of monoalkylated aromatic compounds, particularly ethylbenzene, cumene and sec-butylbenzene, by the liquid or partial liquid phase alkylation of an alkylatable aromatic compound, particularly benzene. More particularly, the present process uses a catalyst composition comprising a porous crystalline material, e.g. a crystalline aluminosilicate, and binder in the ratio of crystal/binder of from about 20/80 to about 60/40.

Methods for producing the catalysts required for use in the present invention comprise those taught in the publications listed below and incorporated herein by reference, modified only by adjusting the compounding or extrusion, for example, of the final catalyst to comprise a crystal/binder ratio of from about 20/80 to about 60/40. This is well within the ability of those skilled in catalyst manufacturing art. For example, U.S. Pat. No. 4,954,325 describes crystalline MCM-22 and catalyst comprising same, U.S. Pat. No. 5,236,575 describes crystalline MCM-49 and catalyst comprising same, and U.S. Pat. No. 5,362,697 describes crystalline MCM-56 and catalyst comprising same. In compounding or extruding the particular crystalline material with binder to form the catalyst required for use herein, care is taken to do so such that the final catalyst product comprises a crystal/binder ratio of from about 20/80 to about 60/40.

The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a particularly useful feed for the alkylation process of this invention.

The alkylating agents that may be useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products that may be obtained from the process of the present invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butene. Particularly preferred process mechanisms of the invention relate to the production of cumene by the alkylation of benzene with propylene, and production of ethylbenzene by the alkylation of benzene with ethylene.

The reactants for the present improved process can be in partially or completely liquid phase and can be neat, i.e. free from intentional admixture or MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

In the reaction mechanism of the present invention, the alkylation reactor effluent may contain excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure of zeolite Beta, zeolite Y, mordenite or an MCM-22 family material having an X-ray diffraction pattern including d-spacing maxima at 12.4±0.25, 6.9±0.15, 3.57±0.07 and 3.42±0.07 Angstroms.

The X-ray diffraction data used to characterize said above catalyst structures are obtained by standard techniques using the K-alpha doublet of copper as the incident radiation and a diffractometer equipped with a scintillation counter and associated computer as the collection system. Materials having the above X-ray diffraction lines include, for example, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The small crystal TEA-mordenite desired for transalkylation can be produced by crystallization from a synthesis mixture having a molar composition within the following ranges:

|  | Useful | Preferred |
|---|---|---|
| R/R+Na+ = | >0.4 | 0.45-0.7 |
| OH—/SiO2 = | <0.22 | 0.05-0.2 |
| Si/Al2 = | >30-90 | 35-50 |
| H2O/OH = | 50-70 | 50-60 |

The crystallization of small crystal TEA-mordenite from this synthesis mixture is conducted at a temperature of 90 to 200° C., for a time of 6 to 180 hours.

The catalyst for use in the present invention will include an inorganic oxide material matrix or binder. Such matrix or binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

For the improvement of the present invention, relative proportions of the crystalline molecular sieve and binder or matrix may vary narrowly with the ratio of crystal/binder of from about 20/80 to about 60/40.

The catalyst for use in the present invention, or its crystalline molecular sieve component, may or may not contain added functionalization, such as, for example, a metal of Group VI (e.g. Cr and Mo), Group VII (e.g. Mn and Re) or Group VIII (e.g. Co, Ni, Pd and Pt), or phosphorus.

Non-limiting examples of the invention involving an improved alkylation mechanism are described with reference to the following experiments. In these experiments, catalyst reactivity was measured by the following procedure.

Equipment

A 300 ml Parr batch reaction vessel equipped with a stir rod and static catalyst basket was used for the activity and selectivity measurements. The reaction vessel was fitted with two removable vessels for the introduction of benzene and propylene respectively.

Feed Pretreatment

Benzene

Benzene was obtained from a commercial source. The benzene was passed through a pretreatment vessel (2 L Hoke vessel) containing equal parts (by volume) molecular sieve 13×, molecular sieve 4A, Engelhard F-24 Clay, and Selexsorb CD (in order from inlet to outlet). All feed pretreatment materials were dried in a 260° C. oven for 12 hours before using.

Propylene

Propylene was obtained from a commercial specialty gases source and was polymer grade. The propylene was passed through a 300 ml vessel containing pretreatment materials in the following order:
  a. 150 ml molecular sieve 5A
  b. 150 ml Selexsorb CD Both guard-bed materials were dried in a 260° C. oven for 12 hours before using.

Nitrogen

Nitrogen was ultra high purity grade and obtained from a commercial specialty gases source. The nitrogen was passed through a 300 ml vessel containing pretreatment materials in the following order:
  a. 150 ml molecular sieve 5A
  b. 150 ml Selexsorb CD Both guard-bed materials were dried in a 260° C. oven for 12 hours before using.

Catalyst Preparation and Loading

A 2 gram sample of catalyst was dried in an oven in air at 260° C. for 2 hours. The catalyst was removed from the oven and immediately 1 gram of catalyst was weighed. Quartz chips were used to line the bottom of a basket followed by loading of 0.5 or 1.0 gram of catalyst into the basket on top of the first layer of quartz. Quartz chips were then placed on top of the catalyst. The basket containing the catalyst and quartz chips was placed in an oven at 260° C. overnight in air for about 16 hours.

The reactor and all lines were cleaned with a suitable solvent (such as toluene) before each experiment. The reactor and all lines were dried in air after cleaning to remove all traces of cleaning solvent. The basket containing the catalyst and quartz chips was removed from the oven and immediately placed in the reactor and the reactor was immediately assembled.

Test Sequence

The reactor temperature was set to 170° C. and purged with 100 sccm (standard cubic centimeter) of the ultra high purity nitrogen for 2 hours. After nitrogen purged the reactor for 2 hours, the reactor temperature was reduced to 130° C., the nitrogen purge was discontinued and the reactor vent closed. A 156.1 gram quantity of benzene was loaded into a 300 ml transfer vessel, performed in a closed system. The benzene vessel was pressurized to 790 kPa-a (100 psig) with the ultra high purity nitrogen and the benzene was transferred into the reactor. The agitator speed was set to 500 rpm and the reactor was allowed to equilibrate for 1 hour. A 75 ml Hoke transfer vessel was then filled with 28.1 grams of liquid propylene and connected to the reactor vessel, and then connected with 2169 kPa-a (300 psig) ultra high purity nitrogen. After the one-hour benzene stir time had elapsed, the propylene was transferred from the Hoke vessel to the reactor. The 2169 kPa-a (300 psig) nitrogen source was maintained connected to the propylene vessel and open to the reactor during the entire run to maintain constant reaction pressure during the test. Liquid product samples were taken at 30, 60, 120, 150, 180 and 240 minutes after addition of the propylene.

In the Examples below, selectivity is the ratio of recovered product diisopropylbenzene to recovered product isopropylbenzene (DIPB/IPB) after propylene conversion reached 100%. The activity of some examples is determined by calculating the 2nd order rate constant using mathematical techniques known to those skilled in the art.

EXAMPLE 1

Catalyst comprising MCM-49 and alumina binder in the crystal/binder ratio of 80/20 was prepared by extrusion as a 1.27 mm (½0th inch) quadrulobe extrudates.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 199. The selectivity (DIPB/IPB) was 16.4%.

EXAMPLE 2

Catalyst comprising MCM-49 and alumina binder in the crystal/binder ratio of 60/40 was also prepared by extrusion as a 1.27 mm (½0th inch) quadrulobe in the same manner as the catalyst for Example 1.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 236. The selectivity (DIPB/IPB) was 14.3%.

The process of Example 2 showed a 12.8% improvement in DIPB/IPB selectivity and an 18.6% improvement in activity relative to the parent process of Example 1.

EXAMPLE 3

Catalyst comprising MCM-49 and alumina binder in the crystal/binder ratio of 40/60 was also prepared by extrusion as a 1.27 mm (1/20th inch) quadrulobe in the same manner as the catalyst for Example 1.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 106. The selectivity (DIPB/IPB) was 10.2%.

The process of Example 3 showed a 37.8% improvement in DIPB/IPB selectivity relative to the parent process of Example 1 while activity remained within 47% of that of the parent process.

EXAMPLE 4

Catalyst comprising MCM-49 and alumina binder in the crystal/binder ratio of 20/80 was prepared by extrusion as a 1.27 mm (1/20th inch) quadrulobe extrudate in the same manner as the catalyst for Example 1.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 185. The selectivity (DIPB/IPB) was 8.6%.

The process of Example 4 showed an improvement in DIPB/IPB selectivity relative to the parent process of Example 1 of 48%, while activity remained within about 1% of that of the parent.

EXAMPLE 5

Catalyst comprising self-bound MCM-22 (therefore a crystal/binder ratio of 100/0) was prepared by extrusion as a 1.59 mm (1/16th inch) cylindrical extrudate.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 295. The selectivity (DIPB/IPB) was 26.9%.

EXAMPLE 6

Catalyst comprising MCM-22 and alumina binder in the crystal/binder ratio of 80/20 was prepared by extrusion as 1.59 mm (1/16th inch) cylindrical extrudate in the same manner as the catalyst for Example 5.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 184. The selectivity (DIPB/IPB) was 14.0%.

EXAMPLE 7

Catalyst comprising MCM-22 and alumina binder in the crystal/binder ratio of 65/35 was prepared by extrusion as 1.59 mm (1/16th inch) cylindrical extrudate in the same manner as the catalyst for Example 5.

A 0.5 gram quantity of the catalyst of this example was placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). Activity determined by calculating the 2nd order rate constant was 222. The selectivity (DIPB/IPB) was 13.7%.

EXAMPLE 8

Catalyst comprising MCM-22 and alumina binder in the crystal/binder ratio of 60/40 is prepared by extrusion as 1.59 mm (1/16th inch) cylindrical extrudate in the same manner as the catalyst for Example 5.

A 0.5 gram quantity of the catalyst of this example is placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). The selectivity (DIPB/IPB) is about 9.5%, an improvement of from about 31% to about 65% over the processes of Examples 5, 6 and 7.

EXAMPLE 9

Catalyst comprising MCM-22 and alumina binder in the crystal/binder ratio of 40/60 is prepared by extrusion as 1.59 mm (1/16th inch) cylindrical extrudate in the same manner as the catalyst for Example 5.

A 0.5 gram quantity of the catalyst of this example is placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). The selectivity (DIPB/IPB) is about 4.5%, an improvement of from about 67% to about 83% over the processes of Examples 5, 6 and 7.

EXAMPLE 10

Catalyst comprising MCM-22 and alumina binder in the crystal/binder ratio of 20/80 is prepared by extrusion as 1.59 mm (1/16th inch) cylindrical extrudate in the same manner as the catalyst for Example 5.

A 0.5 gram quantity of the catalyst of this example is placed in the batch reactor as described in the catalyst reactivity testing procedure above at a 260° C. pretreatment temperature and contacted with 3 parts benzene and 1 part propylene on a molar basis at a temperature of 130° C. and pressure of 2169 kPa-a (300 psig). The selectivity (DIPB/IPB) is about 0.5%, an improvement of from about 96% to about 98% over the processes of Examples 5, 6 and 7.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. In a process for alkylation of feedstock comprising at least one alkylatable aromatic compound and an alkylating agent to an alkylation product comprising an alkylaromatic compound which comprises contacting said feedstock in at least partial liquid phase under catalytic alkylation conditions including a temperature of from about 0° C. to about 500° C., a pressure of from about 20 to about 25000 kPa-a, a molar ratio of alkylatable aromatic compound to alkylating agent of from about 0.1:1 to about 50:1, and a feed weight hourly space velocity (WHSV) based on the alkylating agent of from about 0.1 to about 500 hr$^{-1}$, with a catalyst composition comprising crystalline MCM-22 or MCM-49 zeolite and an alumina binder having a ratio of crystal/binder of from about 20/80 to about 60/40; wherein the dialkylbenzene to monoalkylbenzene selectivity is less than about 14%.

2. The process of claim 1 wherein said alkylation conditions include a temperature of from about 10° C. to about 260° C., a pressure of from about 100 kPa-a to about 5500 kPa-a, a molar ratio of alkylatable aromatic compound to alkylating agent of from about 0.5:1 to about 10:1, and a feed weight hourly space velocity (WHSV) based on the alkylating agent of from about 0.5 to about 100 hr$^{-1}$.

3. The process of claim 1 wherein said feedstock comprises reformate.

4. The process of claim 1 wherein said feedstock aromatic compound is benzene and said alkylating agent is selected from the group consisting of ethylene, propylene and butenes.

5. The process of claim 1 wherein said feedstock aromatic compound is benzene and said alkylating agent is ethylene, said alkylation product comprises ethylbenzene, and said alkylation conditions include a temperature of from about 150° C. to about 300° C., a pressure up to about 20400 kPa-a, a weight hourly space velocity (WHSV) based on the ethylene alkylating agent of from about 0.1 to about 20 hr$^{-1}$, and a ratio of benzene to ethylene in the alkylation reactor of from about 0.5:1 to about 30:1 molar.

6. The process of claim 1 wherein said feedstock aromatic compound is benzene and said alkylating agent is propylene, said alkylation product comprises cumene, and said alkylation conditions include a temperature of up to about 250° C., a pressure of about 25000 kPa-a or less, a weight hourly space velocity (WHSV) based on propylene alkylating agent of from about 0.1 hr$^{-1}$ to about 250 hr$^{-1}$, and a ratio of benzene to propylene in the alkylation reactor of from about 0.5:1 to about 30:1 molar.

7. The process of claim 1 wherein said feedstock aromatic compound is benzene and said alkylating agent is butenes, said alkylation product comprises butylbenzene, and said alkylation conditions include a temperature of up to about 250° C., a pressure of about 25000 kPa-a or less, a weight hourly space velocity (WHSV) based on butenes alkylating agent of from about 0.1 hr$^{-1}$ to about 250 hr$^{-1}$, and a ratio of benzene to butenes in the alkylation reactor of from about 0.5:1 to about 30:1 molar.

* * * * *